United States Patent
Yang et al.

(10) Patent No.: US 6,649,159 B2
(45) Date of Patent: Nov. 18, 2003

(54) WHOLE-BODY OPTICAL IMAGING OF GENE EXPRESSION AND USES THEREOF

(75) Inventors: Meng Yang, San Diego, CA (US); Eugene Baranov, San Diego, CA (US)

(73) Assignee: AntiCancer, Inc., San Diego, CA (US)

( * ) Notice: Subject to any disclaimer, the term of this patent is extended or adjusted under 35 U.S.C. 154(b) by 0 days.

(21) Appl. No.: 09/812,710

(22) Filed: Mar. 19, 2001

(65) Prior Publication Data

US 2002/0013954 A1 Jan. 31, 2002

Related U.S. Application Data

(60) Provisional application No. 60/190,196, filed on Mar. 17, 2000.

(51) Int. Cl.[7] ................ A61K 48/00; A61K 49/00; A01N 63/00; C12N 15/63; C12N 15/85
(52) U.S. Cl. ................ 424/93.21; 424/93.1; 424/93.2; 424/9.1; 435/320.1; 435/325
(58) Field of Search ............ 800/8; 435/320.1, 435/325; 536/24.5; 424/93.1

(56) References Cited

U.S. PATENT DOCUMENTS

| | | | |
|---|---|---|---|
| 5,650,135 A | 7/1997 | Contag et al. | 424/9.1 |
| 5,876,711 A | 3/1999 | Fattaey | 424/932 |
| 6,020,192 A | 2/2000 | Muzyczka et al. | 435/320.1 |

OTHER PUBLICATIONS

Yang et al., Whole–body optical imaging of green fluorescent protein–expressing tumors and metastates, 2000, PNAS, vol. 97, pp. 1206–1211.*

Edinger et al., Noninvasive assessment of tumor cell proliferation in animal models, 1999, NEOPLASIA, vol. 1, pp. 303–310.*

Zhang et al., An enhanced green fluorescent protein allows sensitive detection of gene transfer in mammalian cells, 1996, Biochemical and Biophysical Communications, vol. 227, pp. 707–711.*

Yang, M. et al. "Whole–Body Optical Imaging of Green Fluorescent Protein–Expressing Tumors and Metastases" PNAS 97(3): 1206–1211 (2000).

Yang, M. et al. "Visualizing Gene Expression by Whole–Body Fluorescence Imaging" PNAS 97(22):12278–12282 (2000).

Benard et al., J. Nucl. Med. (1999) 40(8):1257–1263.
Brenner et al., Eur. J. Nucl. Med. (1999) 26(12):1567–1571.
Engelson et al., Am. J. Clin. Nutr. (1999) 69(9):1162–1169.
Eustace et al., Magn. Reson. Imaging Clin. (N. Am.) (1999) 7(2):209–236.
Jerusalem et al., Blood (1999) 9492):429–433.
Saunders et al., Ann. Thorac. Surg. (1999) 67(3):790–797.
Valk et al., Arch. Surg. (1999) 134(5):503–511.
Yang et al., Proc. Natl. Acad. Sci. USA (2000) 97(3):1206–1211.

* cited by examiner

Primary Examiner—Anne-Marie Falk
Assistant Examiner—Celine Qian
(74) Attorney, Agent, or Firm—Morrison & Foerster LLP

(57) ABSTRACT

The invention relates to the whole-body external optical imaging of gene expression. Specifically, methods for whole-body external optical imaging of gene expression and methods for evaluating a candidate protocol or drug for treating diseases or disorders using a fluorophore operatively linked to the promoter of a gene and external optical imaging are provided herein. Methods to screen for substances or genes that regulate target promoters are also provided.

13 Claims, 2 Drawing Sheets

WHOLE-BODY OPTICAL IMAGING OF GENE EXPRESSION AND USES THEREOF

This application claims priority under 35 U.S.C. 119 from provisional application U.S. Ser. No. 60/190,196 filed Mar. 17, 2000, the contents of which are incorporated herein by reference.

TECHNICAL FIELD

The invention relates to the whole-body external optical imaging of gene expression. Specifically, methods for whole-body external optical imaging of gene expression and methods for evaluating a candidate protocol or drug for treating diseases or disorders using a fluorophore operatively linked to the promoter of a gene and external optical imaging are provided herein. Methods to screen for substances or genes that regulate target promoters are also provided.

BACKGROUND ART

Whole-body imaging technology has been used to monitor "tracer molecules" in the intact body. For example, Brenner et al. studied the diagnostic value of iodine-123-2-hydroxy-3-iodo-6-methoxy-N-[(1-ethyl-2-pyrrolidinyl)methyl] benzamide (IBZM) whole-body imaging in comparison to thallium-201 scintigraphy in patients with metastatic malignant melanoma (Brenner et al., *Eur. J. Nucl. Med.*, 26(12):1567–71 (1999)). Benard et al. conducted clinical evaluation of processing techniques for attenuation correction with $^{137}$Cs in whole-body PET imaging (Benard et al., *J. Nucl. Med.*, 40(8):1257–63 (1999)). Jerusalem et al. showed that whole-body positron emission tomography using $^{18}$F-fluorodeoxyglucose for posttreatment evaluation in Hodgkin's disease and non-Hodgkin's lymphoma has higher diagnostic and prognostic value than classical computed tomography scan imaging (Jerusalem et al., *Blood*, 94(2):429–33 (1999)). Eustace et al. discussed practical issues, clinical applications, and future directions of whole-body MR imaging (Eustace et al., *Magn. Reson. Imaging Clin. (N. Am)*, 7(2):209–36 (1999)). Engelson et al. studied fat distribution in HIV-infected patients reporting truncal enlargement quantified by whole-body magnetic resonance imaging (Engelson et al., *Am. J. Clin. Nutr.*, 69(6 :1162–9 (1999)). Valk et al. used whole-body positron emission tomography (PET) imaging with [$^{18}$F]fluorodeoxyglucose in management of recurrent colorectal cancer (Valk et al., Arch. Surg., 134(5):503–11 (1999)). Saunders et al. evaluated fluorine-18-fluorodeoxyglucose whole body positron emission tomography imaging in the staging of lung cancer (Saunders et al., *Ann. Thorac. Surg.*, 67(3):790–7 (1999)).

U.S. Pat. No. 5,650,135 discloses a noninvasive method for detecting the localization of an entity under study from within a mammalian subject, which method comprises: (a) administering to the subject a conjugate of the entity and a light-generating moiety or a transformed cell expressing the light-generating moiety; (b) after a period of time in which the conjugate or transformed cell can achieve localization in the subject, immobilizing the subject within the detection field of a photodetector device; (c) maintaining the subject in an immobilized condition, (d) during said maintaining, measuring photon emission from the light-generating moiety, localized in the subject, with the photodetector device until an image of photon emission can be constructed; and (e) detecting said image through an opaque tissue of said mammal. U.S. Pat. No. 5,650,135 also discloses a noninvasive method for detecting the level of an entity under study in a mammalian subject over time, which method comprises: (a) administering to the subject a conjugate of the entity and a light-generating moiety or a transformed cell expressing the light-generating moiety; (b) placing the subject within the detection field of a photodetector device; (c) maintaining the subject in the detection field of the device; (d) during said maintaining, measuring photon emission from the light-generating moiety, in the subject, with the photodetector device; and (e) repeating steps (b) through (d) at selected intervals, wherein said repeating is effective to detect changes in the level of the entity in the subject over time.

Recently, Yang et al. conducted whole-body optical imaging of green fluorescent protein-expressing tumors and metastases (Yang et al., *Proc. Natl. Acad. Sci. (USA)*, 97(3): 1206–11 (2000)). Yang et al. have imaged, in real time, fluorescent tumors growing and metastasizing in live mice. The whole-body optical imaging system is external and noninvasive. It affords unprecedented continuous visual monitoring of malignant growth and spread within intact animals. Yang et al. have established new human and rodent tumors that stably express very high levels of the Aequorea victoria green fluorescent protein (GFP) and transplanted these to appropriate animals. B16F0-GFP mouse melanoma cells were injected into the tail vein or portal vein of 6-week-old C57BL/6 and nude mice. Whole-body optical images showed metastatic lesions in the brain, liver, and bone of B 16F0-GFP that were used for real time, quantitative measurement of tumor growth in each of these organs. The AC3488-GFP human colon cancer was surgically implanted orthotopically into nude mice. Whole-body optical images showed, in real time, growth of the primary colon tumor and its metastatic lesions in the liver and skeleton. Imaging was with either a trans-illuminated epifluorescence microscope or a fluorescence light box and thermoelectrically cooled color charge-coupled device camera. The depth to which metastasis and micrometastasis could be imaged depended on their size. A 60-micrometer diameter tumor was detectable at a depth of 0.5 mm whereas a 1, 800-micrometer tumor could be visualized at 2.2-mm depth. The simple, noninvasive, and highly selective imaging of growing tumors, made possible by strong GFP fluorescence, enables the detailed imaging of tumor growth and metastasis formation. This should facilitate studies of modulators of cancer growth including inhibition by potential chemotherapeutic agents.

Methods for monitoring gene expression are known in the art (see generally, Ausubel et al. (Ed.), Current Protocols in Molecular Biology, John Wiley & Sons, Inc.). However, whole-body external optical imaging of gene expression, which offers simple, noninvasive, highly selective, and real-time recording and analysis of gene expression in an intact multi-cellular organisms, e.g., animals, is not available currently. The present invention addresses this and other related needs in the art.

DISCLOSURE OF THE INVENTION

The invention provides for whole-body external optical imaging of gene expression and methods for evaluating a candidate protocol or drug for treating diseases or disorders. The method uses a fluorophore operatively linked to the promoter of a gene and external optical imaging. Methods to screen for substances or genes that regulate target promoters are also provided.

In a specific embodiment, a method to monitor the expression of a gene is provided, which method comprises: a) delivering to a multi-cellular organism a nucleic acid encoding a fluorophore operatively linked to the promoter of a gene whose expression is to be analyzed or delivering a cell containing said nucleic acid; and b) observing the presence, absence or intensity of the fluorescence generated by said fluorophore at various locations in said organism by whole-body external fluorescent optical imaging, whereby the expression of said gene is monitored.

In a preferred embodiment, a nucleic acid encoding a fluorophore operatively linked to the promoter of the gene is delivered directly to the organism. Also preferably, the nucleic acid encoding a fluorophore operatively linked to the promoter of the gene is in a viral vector such as a viral vector derived from adenovirus or a lentivirus.

In another preferred embodiment, a cell containing a nucleic acid encoding a fluorophore operatively linked to the promoter of the gene is delivered to the organism. More preferably, the cell is delivered to the organism via a surgical procedure such as direct implantation by surgical orthotopic implantation (SOI) at a desired site.

In still another preferred embodiment, the fluorophore operatively linked to the promoter of a gene is a humanized fluorophore. Also preferably, the fluorophore is a green fluorescent protein (GFP), a blue fluorescent protein (BFP) or a red fluorescent protein (RFP). More preferably, the GFP is the humanized hGFP-S65T.

In yet another preferred embodiment, the multi-cellular organism to be analyzed is a plant or an animal, including a transgenic animal. More preferably, the animal is a mammal. A human can also be analyzed by the present method.

In yet another preferred embodiment, the gene to be analyzed is expressed in a tissue or organ specific manner. More preferably, the gene is expressed in connective, epithelium, muscle or nerve tissue. Also more preferably, the gene is expressed in an internal animal organ such as brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels, etc. Yet more preferably, the gene to be analyzed is a tumor or cancer associated gene such as an oncogene or a tumor suppressor gene.

In yet another preferred embodiment, the expression of more than one gene is monitored simultaneously.

In another specific embodiment, a method to evaluate a candidate protocol or drug for treating a disease or disorder is provided, which method comprises: a) administering said protocol or drug to a non-human mammalian subject which expresses a fluorophore under the direction of a promoter of a gene associated with a disease or disorder, and determining the expression of said promoter via observing the presence, absence or intensity of the fluorescence generated by said fluorophore at various locations in said mammalian subject by whole-body external fluorescent optical imaging; b) determining the expression of said promoter, via observing the presence, absence or intensity of the fluorescence generated by said fluorophore at various locations in said mammalian subject by whole-body external fluorescent optical imaging, in a control non-human mammalian subject which expresses said fluorophore under the direction of said promoter of said gene; and c) comparing the expression of said promoter determined in steps a) and b), wherein the expression determined in step a) is different from that in step b) identifies said protocol or drug as effective in treating the disease or disorder.

If overexpression of the gene is associated with the disease or disorder, the expression determined in step a) is lower than that in step b) when said protocol or drug is effective in treating the disease or disorder.

If underexpression of the gene is associated with the disease or disorder, the expression determined in step a) is higher than that in step b) when said protocol or drug is effective in treating the infection.

Preferably, the disease or disorder is a cancer, an immune system disease or disorder, a metabolism disease or disorder, a muscle and bone disease or disorder, a nervous system disease or disorder, a signal disease or disorder, or a transporter disease or disorder.

Preferably, the non-human mammalian subject which expresses a fluorophore under the direction of a promoter of the gene is produced by delivering a nucleic acid encoding the fluorophore operatively linked to the promoter of the gene, or a cell containing the nucleic acid, to the non-human mammalian subject. Alternatively, the non-human mammalian subject used in the screen is a transgenic animal.

The non-human mammalian subject used in the screening is preferably a well established laboratory animal such as a mice, a rabbit or a non-human primate.

The fluorophore used in the screening is preferably a green fluorescent protein (GFP), a blue fluorescent protein (BFP) or a red fluorescent protein (RFP).

More than one candidate protocol or candidate drug is preferably screened for simultaneously.

If the non-human mammalian subject expresses a fluorophore under the direction of a promoter of an infectious organism, the expression determined in step a) is lower than that in step b) when said protocol or drug is effective in treating infection caused by the infectious organism.

The non-human mammalian subject used in the screening is preferably an infectious disease animal model.

The infectious organism screened against is preferably a fungus such as a yeast, a bacterium such as an eubacteria or an archaebacteria, or a virus such as a Class I virus, a Class II virus, a Class III virus, a Class IV virus, a Class V virus or a Class VI virus.

If the infection is caused by a bacterium, the candidate drug to be screened is preferably an antibiotic.

In still another specific embodiment, a method to screen for a modulator of the expression of a gene in a non-human multi-cellular organism is provided, which method comprises: a) administering a test substance to a non-human multi-cellular organism which expresses a fluorophore under the direction of a promoter of a gene, and determining the expression of said promoter via observing the presence, absence or intensity of the fluorescence generated by said fluorophore at various locations in said multi-cellular organism by whole-body external fluorescent optical imaging; b) determining the expression of said promoter, via observing the presence, absence or intensity of the fluorescence generated by said fluorophore at various locations by whole-body external fluorescent optical imaging, in a control multi-cellular organism which expresses said fluorophore under the direction of said promoter of said gene; and c) comparing the expression of said promoter determined in steps a) and b), wherein the expression determined in step a) is different from that in step b) identifies said test substance as a modulator of said gene expression. Preferably, the promoter is an endogenous promoter of the multi-cellular organism.

In yet another specific embodiment, a method to screen for a non-human multi-cellular organism that expresses a gene at an altered level is provided, which method comprises: a) administering a mutation-inducing agent or treatment to a non-human multi-cellular organism which expresses a fluorophore under the direction of a promoter of a gene, and determining the expression of said promoter via observing the presence, absence or intensity of the fluorescence generated by said fluorophore at various locations in said multi-cellular organism by whole-body external fluorescent optical imaging; b) determining the expression of said promoter, via observing the presence, absence or intensity of the fluorescence generated by said fluorophore at various locations by whole-body external fluorescent optical imaging in an untreated control multi-cellular organism which expresses said fluorophore under the direction of said promoter of said gene; and c) comparing the expression of said promoter determined in steps a) and b), wherein the expression determined in step a) is different from that in step b) identifies a multi-cellular organism that expresses said gene at the altered level. Preferably, the mutation-inducing agent or treatment causes a mutation in germ-line cells of the multi-cellular organism so that the desired mutation is stably-transferable to offspring of the multi-cellular organism.

BRIEF DESCRIPTION OF THE DRAWINGS

FIG. 2A is a diagram of lentiviral vector GFP-LV. FIG. 2B is a diagram of a control observation method; whole body measurement involved use of a light box.

MODES FOR CARRYING OUT THE INVENTION

A. Definitions

Figure 1A:
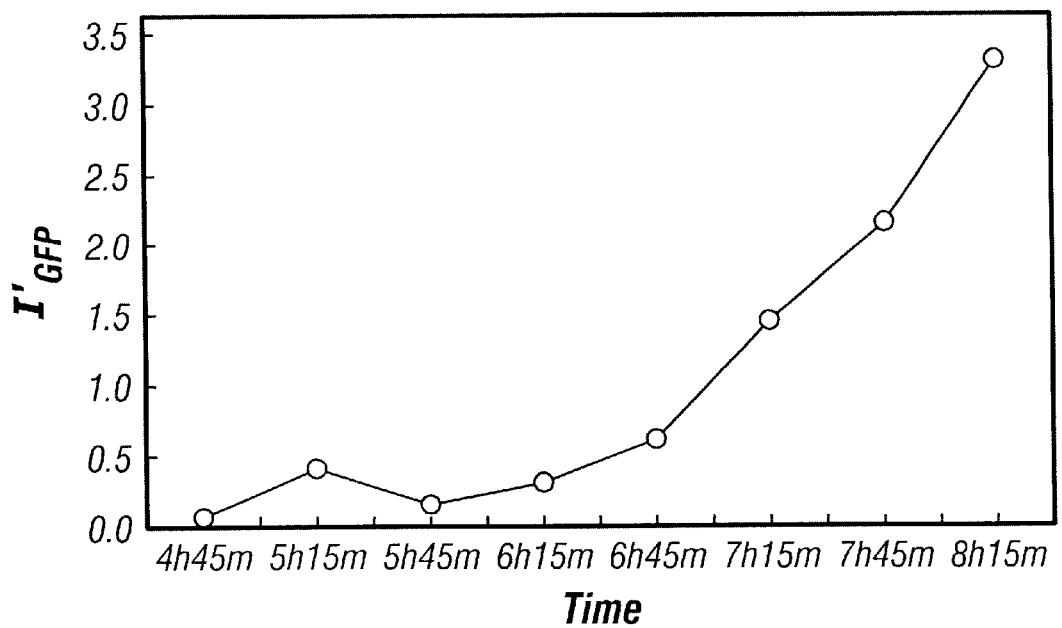
FIGS. 1A and 1B show the time course of expression of adenoviral-administered GFP in brain and liver respectively. Fluorescence first becomes visible in the brain within six (6) hours after local delivery and liver fluorescence became detectable at about seven (7) hours after injection into the tail vein.

Unless defined otherwise, all technical and scientific terms used herein have the same meaning as is commonly understood by one of ordinary skill in the art to which this invention belongs. All patents, applications, published applications and other publications and sequences from GenBank and other data bases referred to herein are incorporated by reference in their entirety.

As used herein, "delivering a nucleic acid to a multi-cellular organism" refers to a process in which the nucleic acid is either administered directly into the body of the multi-cellular organism, or the nucleic acid is administered into a cell first, and then the cell containing the nucleic acid is administered into the body of the multi-cellular organism. After delivery into the organism, the nucleic acid may exist independently from the genome of the host organism or may be integrated into the genome of the host organism. If the nucleic acid is integrated into a germline cell of the host organism, such nucleic acid may be transmitted into the host organism's offspring.

As used herein, "whole-body external fluorescent optical imaging" refers to an imaging process in which the presence, absence or intensity of the fluorescence generated by the fluorophore at various locations in the host organism is monitored, recorded and/or analyzed externally without any procedure, e.g., surgical procedure, to expose and/or to excise the desired observing site from the host organism. To achieve the whole-body external fluorescent optical imaging, it is necessary that the intensity of the fluorescence generated by the fluorophore is sufficiently high so that, even when the fluorescence site is an internal one within the host organism body, the fluorescence signal can be analyzed externally without exposing or excising the site from the host body, or while the animal is not controlled.

As no invasive procedures are required and the intensity of the signal is sufficiently great for direct observation, the animal may remain completely mobile and need not be restrained. The ability to provide a completely non-invasive observation protocol is highly significant. If the animal is traumatized either by, e.g., incision or by physical restraint, e.g., straps or pins, the alteration in metabolism may affect the expression of the genes in organs or tissues.

Since whole-body external fluorescent optical imaging are quick and easily amenable to automation, it can be used for monitoring large number of gene expression simultaneously. In addition, it can be employed in high-throughput screening methods for identifying protocols, substances including candidate drugs, and cis-acting regulators that regulate the expression of a target gene. Using the whole-body external fluorescent optical imaging provided in this application, multiple candidate protocols, substances, drugs, and cis-acting regulators can be screened for, either against a single target gene or against multiple target genes, in either a single animal or in multiple animals, simultaneously.

As used herein, "fluorophore" refers to a protein that is auto-fluorescent such that no other substrates or co-factors are needed for it to fluoresce. Non-limiting examples of such fluorophores include green fluorescent proteins (GFPs), blue fluorescent proteins (BFPs) and red fluorescent protein (RFPs), and functional fragments, derivatives and analogues thereof.

As used herein, "a promoter region or promoter element" refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated.

As used herein, "operatively linked or operationally associated" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, e.g., Kozak, *J. Biol. Chem.*, 266:19867–19870 (1991)) can be inserted immediately 5' of the start codon and may enhance expression. The desirability of (or need for) such modification may be empirically determined.

As used herein, "humanized fluorophore" refers to a fluorophore whose codon is modified according to the codon usage pattern in human genome to enhance its expression while substantially maintaining its fluorescent characteristics.

As used herein, "multi-cellular organism" refers to an organism with certain cell numbers, mass, and internal structure so that internal sites of such multi-cellular organism are not externally detectable by non-fluorescent optical imaging without exposing the internal sites. Sufficiently high intensity of internal fluorescence is needed for external fluorescent optical imaging of the internal site.

As used herein, "plant" refers to any of various photosynthetic, eucaryotic multi-cellular organisms of the kingdom Plantae, characteristically producing embryos, containing chloroplasts, having cellulose cell walls and lacking locomotion.

As used herein, "animal" refers to a multi-cellular organism of the kingdom of Animalia, characterized by a capacity for locomotion, nonphotosynthetic metabolism, pronounced response to stimuli, restricted growth and fixed bodily structure. Non-limiting examples of animals include birds such as chickens, vertebrates such fish and mammals such as mice, rats, rabbits, cats, dogs, pigs, cows, ox, sheep, goats, horses, monkeys and other non-human primates.

As used herein, "expressed in a tissue or organ specific manner" refers to a gene expression pattern in which a gene is expressed, either transiently or constitutively, only in certain tissues or organs, but not in other tissues or organs.

As used herein, "tissue" refers to a collection of similar cells and the intracellular substances surrounding them. There are four basic tissues in the body: 1) epithelium; 2) connective tissues, including blood, bone, and cartilage; 3) muscle tissue; and 4) nerve tissue.

As used herein, "organ" refers to any part of the body exercising a specific function, as of respiration, secretion or digestion.

As used herein, "disease or disorder" refers to a pathological condition in an organism resulting from, e.g., infection or genetic defect, and characterized by identifiable symptoms.

As used herein, neoplasm (neoplasia) refers to abnormal new growth, and thus means the same as tumor, which may be benign or malignant. Unlike hyperplasia, neoplastic proliferation persists even in the absence of the original stimulus.

As used herein, cancer refers to a general term for diseases caused by any type of malignant tumor.

As used herein, "oncogene" refers to a mutated and/or overexpressed version of a normal gene of animal cells (the proto-oncogene) that in a dominant fashion can release the cell from normal restraints on growth, and thus alone, or in concert with other changes, convert a cell into a tumor cell. Exemplary oncogenes include, but are not limited to, abl, erbA, erbB, ets, fes (fps), fgr, fms, fos, hst, int1, int2, jun, hit, B-lym, mas, met, mil (raf), mos, myb, myc, N-myc, neu (ErbB2), ral (mil), Ha-ras, Ki-ras, N-ras, rel, ros, sis, src, ski, trk and yes.

As used herein, "tumor suppressor gene" (or anti-oncogene, cancer susceptibility gene) refers to a gene that encodes a product which normally negatively regulates the cell cycle, and which must be mutated or otherwise inactivated before a cell can proceed to rapid division. Exemplary tumor suppressor genes include, but are not limited to, p16, p21, p53, RB (retinoblastoma), WT-1 (Wiln's tumor), DCC (deleted in colonic carcinoma), NF-1 (neurofibrosarcoma) and APC (adenomatous polypospis coli).

As used herein, "an immune system disease or disorder" refers to a pathological condition caused by a defect in the immune system. The immune system is a complex and highly developed system, yet its mission is simple: to seek and kill invaders. If a person is born with a severely defective immune system, death from infection by a virus, bacterium, fungus or parasite will occur. In severe combined immunodeficiency, lack of an enzyme means that toxic waste builds up inside immune system cells, killing them and thus devastating the immune system. A lack of immune system cells is also the basis for DiGeorge syndrome: improper development of the thymus gland means that T cell production is diminished. Most other immune disorders result from either an excessive immune response or an 'autoimmune attack'. For example, asthma, familial Mediterranean fever and Crohn disease (inflammatory bowel disease) all result from an over-reaction of the immune system, while autoimmune polyglandular syndrome and some facets of diabetes are due to the immune system attacking 'self' cells and molecules. A key part of the immune system's role is to differentiate between invaders and the body's own cells—when it fails to make this distinction, a reaction against 'self' cells and molecules causes autoimmune disease.

As used herein, "a metabolism disease or disorder" refers to a pathological condition caused by errors in metabolic processes. Metabolism is the means by which the body derives energy and synthesizes the other molecules it needs from the fats, carbohydrates and proteins we eat as food, by enzymatic reactions helped by minerals and vitamins. There is a significant level of tolerance of errors in the system: often, a mutation in one enzyme does not mean that the individual will suffer from a disease. A number of different enzymes may compete to modify the same molecule, and there may be more than one way to achieve the same end result for a variety of metabolic intermediates. Disease will only occur if a critical enzyme is disabled, or if a control mechanism for a metabolic pathway is affected.

As used herein, "a muscle and bone disease or disorder" refers to a pathological condition caused by defects in genes important for the formation and function of muscles, and connective tissues. Connective tissue is used herein as a broad term that includes bones, cartilage and tendons. For example, defects in fibrillin—a connective tissue protein that is important in making the tissue strong yet flexible—cause Marfan syndrome, while diastrophic dysplasia is caused by a defect in a sulfate transporter found in cartilage. Two diseases that originate through a defect in the muscle cells themselves are Duchenne muscular dystrophy (DMD) and myotonic dystrophy (DM). DM is another 'dynamic mutation' disease, similar to Huntington disease, that involves the expansion of a nucleotide repeat, this time in a muscle protein kinase gene. DMD involves a defect in the cytoskeletal protein, dystrophin, which is important for maintaining cell structure.

As used herein, "a nervous system disease or disorder" refers to a pathological condition caused by defects in the nervous system including the central nervous system, i.e., brain, and the peripheral nervous system. The brain and nervous system form an intricate network of electrical signals that are responsible for coordinating muscles, the senses, speech, memories, thought and emotion. Several diseases that directly affect the nervous system have a genetic component: some are due to a mutation in a single gene, others are proving to have a more complex mode of inheritance. As our understanding of the pathogenesis of neurodegenerative disorders deepens, common themes begin to emerge: Alzheimer brain plaques and the inclusion bodies found in Parkinson disease contain at least one common component, while Huntington disease, fragile X syndrome and spinocerebellar atrophy are all 'dynamic mutation' diseases in which there is an expansion of a DNA repeat sequence. Apoptosis is emerging as one of the molecular mechanisms invoked in several neurodegenerative diseases, as are other, specific, intracellular signaling events. The biosynthesis of myelin and the regulation of cholesterol traffic also figure in Charcot-Marie-Tooth and Neimann-Pick disease, respectively.

As used herein, "a signal disease or disorder" refers to a pathological condition caused by defects in the signal transduction process. Signal transduction within and between cells mean that they can communicate important information and act upon it. Hormones released from their site of synthesis carry a message to their target site, as in the case of leptin, which is released from adipose tissue (fat cells) and transported via the blood to the brain. Here, the leptin signals that enough has been eaten. Leptin binds to a receptor on the surface of hypothalamus cells, triggering subsequent intracellular signaling networks. Intracellular signaling defects account for several diseases, including cancers, ataxia telangiectasia and Cockayne syndrome. Faulty DNA repair mechanisms are also invoked in pathogenesis, since control of cell division, DNA synthesis and DNA repair all are inextricably linked. The end-result of many cell signals is to alter the expression of genes (transcription) by acting on DNA-binding proteins. Some diseases are the result of a lack of or a mutation in these proteins, which stop them from binding DNA in the normal way. Since signaling networks impinge on so many aspects of normal function, it is not surprising that so many diseases have at least some basis in a signaling defect.

As used herein, "a transporter disease or disorder" refers to a pathological condition caused by defects in a transporter, channel or pump. Transporters, channels or pumps that reside in cell membranes are key to maintaining the right balance of ions in cells, and are vital for transmitting signals from nerves to tissues. The consequences of defects in ion channels and transporters are diverse, depending on where they are located and what their cargo is. For example, in the heart, defects in potassium channels do not allow proper transmission of electrical impulses, resulting in the arrhythmia seen in long QT syndrome. In the lungs, failure of a sodium and chloride transporter found in epithelial cells leads to the congestion of cystic fibrosis, while one of the most common inherited forms of deafness, Pendred syndrome, looks to be associated with a defect in a sulphate transporter.

As used herein, "infection" refers to invasion of the body of a multi-cellular organism with organisms that have the potential to cause disease.

As used herein, "infectious organism" refers to an organism that is capable to cause infection of a multi-cellular organism. Most infectious organisms are microorganisms such as viruses, bacteria and fungi.

As used herein, "bacteria" refers to small prokaryotic organisms (linear dimensions of around 1 μm) with non-compartmentalized circular DNA and ribosomes of about 70S. Bacteria protein synthesis differs from that of eukaryotes. Many anti-bacterial antibiotics interfere with bacteria proteins synthesis but do not affect the infected host.

As used herein, "eubacteria" refers to a major subdivision of the bacteria except the archaebacteria. Most Gram-positive bacteria, cyanobacteria, mycoplasmas, enterobacteria, pseudomonas and chloroplasts are eubacteria. The cytoplasmic membrane of eubacteria contains ester-linked lipids; there is peptidoglycan in the cell wall (if present); and no introns have been discovered in eubacteria.

As used herein, "archaebacteria" refers to a major subdivision of the bacteria except the eubacteria. There are 3 main orders of archaebacteria: extreme halophiles, methanogens and sulphur-dependent extreme thermophiles. Archaebacteria differs from eubacteria in ribosomal structure, the possession (in some case) of introns, and other features including membrane composition.

As used herein, "virus" refers to obligate intracellular parasites of living but non-cellular nature, consisting of DNA or RNA and a protein coat. Viruses range in diameter from about 20 to about 300 nm. Class I viruses (Baltimore classification) have a double-stranded DNA as their genome; Class II viruses have a single-stranded DNA as their genome; Class III viruses have a double-stranded RNA as their genome; Class IV viruses have a positive single-stranded RNA as their genome, the genome itself acting as mRNA; Class V viruses have a negative single-stranded RNA as their genome used as a template for mRNA synthesis; and Class VI viruses have a positive single-stranded RNA genome but with a DNA intermediate not only in replication but also in mRNA synthesis. The majority of viruses are recognized by the diseases they cause in plants, animals and prokaryotes. Viruses of prokaryotes are known as bacteriophages.

As used herein, "fungi" refers to a division of eucaryotic organisms that grow in irregular masses, without roots, stems, or leaves, and are devoid of chlorophyll or other pigments capable of photosynthesis. Each organism (thallus) is unicellular to filamentous, and possess branched somatic structures (hyphae) surrounded by cell walls containing glucan or chitin or both, and containing true nuclei.

As used herein, "antibiotic" refers to a substance either derived from a mold or bacterium or organically synthesized, that inhibits the growth of certain microorganisms without substantially harming the host of the microorganisms to be killed or inhibited.

As used herein, "test substance" refers to a chemically defined compound (e.g., organic molecules, inorganic molecules, organic/inorganic molecules, proteins, peptides, nucleic acids, oligonucleotides, lipids, polysaccharides, saccharides, or hybrids among these molecules such as glycoproteins, etc.) or mixtures of compounds (e.g., a library of test compounds, natural extracts or culture supernatants, etc.) whose effect on the promoter to be analyzed is determined by the disclosed and/or claimed methods herein.

For clarity of disclosure, and not by way of limitation, the detailed description of the invention is divided into the subsections that follow.

B. Methods of Whole-Body External Optical Imaging of Gene Expression

In a specific embodiment, a method to monitor the expression of a gene is provided herein, which method comprises: a) delivering to a multi-cellular organism a nucleic acid encoding a fluorophore operatively linked to the promoter of a gene whose expression is to be analyzed or a cell containing said nucleic acid; and b) observing the presence, absence or intensity of the fluorescence generated by said fluorophore at various locations in said organism by whole-body external fluorescent optical imaging, whereby the expression of said gene is monitored.

The present methods can be used to monitor gene expression for any suitable purposes including prognostic, diagnostic and screening purposes. For example, if abnormal gene expression is associated with a disease or disorder in a multi-cellular organism such as a plant or an animal, the present method can be used in prognosis or diagnosis by monitoring the abnormal gene expression. The present monitoring methods are advantageous over the currently available gene expression monitoring methods in several aspects. First, the present monitoring methods can avoid any invasive procedures and this is particularly advantageous for human clinical uses. Second, the present monitoring methods offer in vivo, real-time and continuous monitor and analysis of gene expression in plants or animals, which cannot be accomplished using the currently available monitoring methods. Third, the present monitoring methods are quick and easily amenable to automation, which are important for monitoring large number of gene expression simultaneously. Since many diseases or disorders involve abnormal gene expression of more than gene, the present monitoring methods are particularly suitable for the prognosis and diagnosis of these diseases or disorders. Besides prognosis or diagnosis, if expression of certain genes is a good indicator of tissue or organ health or functionality, the present monitoring methods can also be used in monitoring the health or functionality of these tissues or organs without any invasive procedures.

1. Methods for Delivering the Nucleic Acids into the Multi-Cellular Organism

The nucleic acids encoding a fluorophore operatively linked to the promoter of a gene whose expression is to be analyzed can be a DNA or a RNA. Such nucleic acids can be delivered into the body of the multi-cellular organism by any methods known in the art.

For example, if the host multi-cellular organism is an animal, the DNA or RNA sequence can be delivered to the interstitial space of tissues of the animal body, including those of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers or organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation of the lymph fluid of the lymphatic channels.

The DNA or RNA sequence can be conveniently delivered by injection into the tissues comprising these cells. They are preferably delivered to and expressed in persistent, non-dividing cells which are differentiated, although delivery and expression can be achieved in non-differentiated or less completely differentiated cells, such as, for example, stem cells of blood or skin fibroblasts.

In a specific embodiment, the DNA or RNA sequence is delivered directly to a tissue of the host animal. Preferably, the DNA or RNA sequence is delivered directly to muscle, skin or mucous membrane. Delivery to the interstitial space of muscle tissue is preferred because muscle cells are particularly competent in their ability to take up and express polynucleotides.

The DNA or RNA sequence can be delivered directly to a tissue of the host animal by injection, by gene gun technology or by lipid mediated delivery technology. The injection can be conducted via a needle or other injection devices. The gene gun technology is disclosed in U.S. Pat. No. 5,302,509 and the lipid mediated delivery technology is disclosed in U.S. Pat. No. 5,703,055.

In still another specific embodiment, the DNA or RNA sequence is delivered to a cell of host animal and said cell containing the DNA or RNA sequence is delivered to a suitable tissue of the host animal. Preferably, the DNA or RNA sequence is delivered to tail or portal vein of the host animal.

The DNA or RNA sequence can be delivered to the cells of the host animal by a number of methods (see generally Koprowski & Weiner, DNA vaccination/genetic vaccination, 1998. Springer-verlag Berlin Heidelberg) including $Ca_3(PO_4)_2$-DNA transfection (Sambrook et al., *Molecular Cloning*, 2nd Edition, Plainview, N.Y. Cold Spring Harbor Press, 1989), DEAE dextran-DNA transfection (Sambrook et al., *Molecular Cloning*, 2nd Edition, Plainview, N.Y. Cold Spring Harbor Press, 1989), electroporation (e.g., protocols from Bio-Rad), transfection using "LIPOFECTIN"™ reagent (e.g., protocols from BRL-Life Science), gene gun technology (U.S. Pat. No. 5,302,509), or viral gene delivery system (Kaplitt et al., *Viral Vectors, Academic Press, Inc.*, 1995).

Gold-particle based gene gun delivery is disclosed in U.S. Pat. No. 5,302,509. In a specific embodiment, Bio-Rad helios gene gun system is used in the DNA delivery. (BIO-RAD Inc. New England). The helios gene gun is a convenient, hand-held device that provides rapid and direct gene transfer in vivo. The device employs an adjustable, helium pulse to sweep DNA coated gold microcarriers from the inner wall of a small plastic cartridge directly into the target cells. The tubing prepstation and tubing cutter provide a simple way to prepare 50 cartridge "bullets" at a time.

In a preferred embodiment, a nucleic acid encoding a fluorophore operatively linked to the promoter of the gene is delivered directly to the organism. More preferably, the nucleic acid encoding a fluorophore operatively linked to the promoter of the gene is delivered to the organism, or to a cell to be delivered to the organism, in a viral vector such as a viral vector derived from adenovirus or a lentivirus.

Any viral vectors known in the art can be used. For example, vectors derived from a parvovirus (U.S. Pat. Nos. 5,252,479 and 5,624,820), a paramyxovirus such as simian virus 5 (SV5) (U.S. Pat. No. 5,962,274), a retrovirus such as HIV (U.S. Pat. Nos. 5,753,499 and 5,888,767), and a baculovirus such as a nuclear polyhedrosis virus (U.S. Pat. No. 5,674,747) can be used. Preferably, a vector derived from adenovirus can be used (U.S. Pat. Nos. 5,670,488, 5,817, 492, 5,820,868, 5,856,152, 5,981,225).

U.S. Pat. No. 5,670,488 discloses an adenoviral vector comprising an adenovirus genome from which one or more of the E4 open reading frames has been deleted, but retaining sufficient E4 sequences to promote virus replication in vitro, and additionally comprising a DNA sequence of interest operably linked to expression control sequences and inserted into said adenoviral genome.

U.S. Pat. No. 5,817,492 discloses a recombinant adenoviral vector comprising: two DNA sequences which serve as a substrate for a recombinase enzyme, an origin of replication which is operable in an animal cell, a promoter, a foreign gene and a poly(A) sequence, wherein said origin of replication, promoter, foreign gene and poly(A) sequence are located between the two DNA sequences, and wherein said vector contains an E1A gene region deletion.

U.S. Pat. No. 5,820,868 discloses a live recombinant bovine adenovirus vector (BAV) wherein a part or all of the E3 multiple gene coding region is replaced by a heterologous nucleotide sequence encoding a foreign gene or fragment thereof. It also discloses a live recombinant bovine adenovirus vector (BAV) wherein part or all of the E3 multiple gene coding region is replaced by a heterologous nucleotide sequence encoding a foreign gene or fragment thereof and wherein said heterologous nucleotide sequence is optionally under the control of a promoter not normally associated with either said foreign gene or the bovine adenovirus genome.

U.S. Pat. No. 5,856,152 discloses a hybrid viral vector comprising: (a) adenovirus sequences comprising the adenovirus 5'and 3' cis-elements necessary for replication and virion encapsidation; and (b) adeno-associated virus sequences comprising the 5' and 3' ITRs of an adeno-associated virus, said adeno-associated virus sequences flanked by the adenoviral sequences of (a); and (c) a selected gene operatively linked to regulatory sequences which direct its expression in a target cell, said gene and regulatory sequences flanked by the adeno-associated virus sequences of (b).

U.S. Pat. No. 5,981,225 discloses a gene transfer vector consisting essentially of, in 5' to 3' orientation, the following elements: (i) a first adenovirus inverted terminal repeat, (ii) an adenoviral VAI gene and/or VAII gene, (iii) a gene foreign to adenovirus, wherein said gene is operably linked to a promoter functional in adenovirus target cells, and (iv) a second adenovirus inverted terminal repeat, wherein the order of elements (ii) and (iii) may be reversed; and wherein one or both of element (i) and element (iv) additionally comprise an adenovirus packaging signal, and wherein said vector is incapable of producing, in vitro, recombinant adenovirus virus particles which have encapsidated therein said vector unless said vector is co-transfected or co-infected into adenovirus host cells with adenovirus genomic DNA or adenovirus particles containing adenovirus genomic DNA, respectively.

In another preferred embodiment, cells containing a nucleic acid encoding a fluorophore operatively linked to the promoter of the gene are delivered to the organism. More preferably, the cells are delivered to the organism via a surgical procedure such as direct implantation by surgical orthotopic implantation (SOI) at a desired site (see e.g., Chang et al., *Anticancer Res.*, 19(5B):4199 (1999); and An et al., *Prostate,* 34(3 :169–74 (1998)).

It will be understood, that by introducing a nucleic acid molecule wherein a promoter is coupled to a nucleotide sequence encoding a fluorescent reporter gene, the introduced nucleic acid molecule can be used as a surrogate for the endogenous promoter. Thus, if the endogenous gene is over-expressed or under-expressed in the context of a particular condition, the behavior of the introduced construct will mimic that of the endogenous promoter. It is not necessary that the reporter-encoding nucleotide sequence be operably linked only to a promoter; the nucleotide sequence encoding reporter may be introduced into the nucleotide sequence encoding the protein normally under control of the promoter or coupled to another protein. Any method of operably linking the nucleotide sequence encoding reporter to the control sequences for the gene whose expression is to be monitored falls within the scope of the invention.

It will be seen that there are a number of ways to introduce this construct. First, the nucleic acid comprising the reporter encoding nucleotide sequence operably linked to the control sequences/promoter of interest can be introduced to the multicellular organism by direct injection, but preferably using a viral vector, such as a adenoviral vector or a antiviral vector. Since the introduced construct is not endogenous, the expression of this construct essentially functions as a surrogate for the endogenous gene. That is, the same influences which influence the endogenous gene will also influence the introduced construct. Thus, the conclusions reached by observing the expression of the construct, including the effects of various treatments on such expression, can be extrapolated to, and are equally valid for, the counterpart endogenous gene.

Second, the reporter encoding nucleotide sequence could be introduced into the cells of a particular tissue by targeting to the promoter to be studied and inserted using position-specific techniques, such as homologous recombination. When this method is used, the expression of the endogenous promoter can be observed directly as well as can the effect of various treatments thereon.

Third, a construct such as those described for the first method can be provided to embryonic tissue to obtain transgenic organisms where the reporter construct is itself endogenous, see, for example, Fukumura, D., et al., *Cell* (1998) 94:715–725, incorporated herein by reference, which describes transgenic mice which use GFP as a reporter for VEGF promoter activity.

Techniques for all three methods are well known in the art.

2. Fluorophores

Any fluorophores known in the art can be used in the present methods. In a preferred embodiment, the fluorophore operatively linked to the promoter of a gene is a humanized fluorophore. Also preferably, the fluorophore is a green fluorescent protein (GFP), a blue fluorescent protein (BFP) and a red fluorescent protein (RFP). More preferably, the GFP is the humanized hGFP-S65T.

The native gene encoding GFP has been cloned from the bioluminescent jellyfish Aequorea victoria (Morin et al., *J. Cell Physiol.,* 77:313–318 (1972)). The availability of the gene has made it possible to use GFP as a marker for gene expression. GFP itself is a 283 amino acid protein with a molecular weight of 27 kD. It requires no additional proteins from its native source nor does it require substrates or cofactors available only in its native source in order to fluoresce (Prasher et al., *Gene,* 111:229–233 (1992); Yang et al., *Nature Biotechnol.,* 14:1252–1256 (1996); and Cody et al., *Biochemistry,* 32:1212–1218 (1993)). Mutants of the GFP gene have been found useful to enhance expression and to modify excitation and fluorescence. GFP-S65T (wherein serine at 65 is replaced with threonine) is particularly useful in the invention method and has a single excitation peak at 490 nm. (Heim et al., *Nature,* 373:663–664 (1995)); and U.S. Pat. No. 5,625,048). Other mutants have also been disclosed by Delagrade et al., *Biotechnology,* 13:151–154 (1995); Cormack et al., *Gene,* 173:33–38 (1996); and Cramer et al. *Nature Biotechnol.,* 14:315–319 (1996). Additional mutants are also disclosed in U.S. Pat. No. 5,625,048. By suitable modification, the spectrum of light emitted by the GFP can be altered. Thus, although the term "GFP" is used in the present application, the proteins included within this definition are not necessarily green in appearance. Various forms of GFP exhibit colors other than green and these, too, are included within the definition of "GFP" and are useful in the methods and materials of the invention. In addition, it is noted that green fluorescent proteins falling within the definition of "GFP" herein have been isolated from other organisms, such as the sea pansy, *Renilla reriformis.* Any suitable and convenient form of the GFP gene can be used in the invention. Techniques for labeling cells in general using GFP are disclosed in U.S. Pat. No. 5,491,084 (supra).

Other GFP, BFP and RFP can be used in the present methods. For instances, the green fluorescent proteins encoded by nucleic acids with the following GenBank accession Nos. can be used: U47949 (AGP1); U43284; AF007834 (GFPuv); U89686 (*Saccharomyces cerevisiae* synthetic green fluorescent protein (cox3::GFPm-3) gene); U89685 (*Saccharomyces cerevisiae* synthetic green fluorescent protein (cox3::GFPm) gene); U87974 (Synthetic construct modified green fluorescent protein GFP5-ER (mgfp5-ER)); U87973 (Synthetic construct modified green fluorescent protein GFP5 (mgfp5)); U87625 (Synthetic construct modified green fluorescent protein GFP-ER (mfgp4-ER)); U87624 (Synthetic construct green fluorescent protein (mgfp4) mRNA)); U73901 (Aequorea victoria mutant 3); U50963 (Synthetic); U70495 (soluble-modified green fluorescent protein (smGFP)); U57609 (enhanced green fluorescent protein gene); U57608 (enhanced green fluorescent protein gene); U57607 (enhanced green fluorescent protein gene); U57606 (enhanced green fluorescent protein gene); U55763 (enhanced green fluorescent protein (egfp)); U55762 (enhanced green fluorescent protein (egfp); U55761 (enhanced green fluorescent protein (egfp)); U54830 (Synthetic *E. coli* Tn3-derived transposon green fluorescent protein (GF); U36202; U36201; U19282; U19279; U19277; U19276; U19281; U19280; U19278; L29345 (Aequorea victoria); M62654 (Aequorea victoria); M62653 (Aequorea victoria); AAB47853 ((U87625) synthetic construct modified green fluorescent protein (GFP-ER)); AAB47852 ((U87624) synthetic construct green fluorescent protein).

Similarly, the blue fluorescent proteins encoded by nucleic acids with the following GenBank accession Nos. can be used: U70497 (soluble-modified blue fluorescent protein (smBFP); 1BFP (blue variant of green fluorescent protein); AAB16959 (soluble-modified blue fluorescent protein).

Also similarly, the red fluorescent proteins encoded by nucleic acids with the following GenBank accession Nos. can be used: U70496 (soluble-modified red-shifted green fluorescent protein (smRSGFP); AAB16958 (U70496) soluble-modified red-shifted green fluorescent protein).

A fluorophore that changes color with time is reported by Teiskikh, A., et al., *Science* (2000) 290:1585–1588, incorporated herein by reference. This permits tracing time dependent expression.

3. Multi-Cellular Organisms

The present methods can be used in monitoring gene expression in any suitable multi-cellular organisms. In a preferred embodiment, the multi-cellular organism to be analyzed is a plant or an animal, including a transgenic animal. More preferably, the animal is a mammal including a human. Animals that can be analyzed with the present monitoring emthods include, but are not limited to, mice, rats, rabbits, cats, dogs, pigs, cows, ox, sheep, goats, horses, monkeys and other non-human primates.

4. Tissue or Organ Specific Gene Expression

The present methods can be used in monitoring expression of genes that are expressed in a tissue or organ specific manner. The present methods can be used in monitoring health and/or functionality of tissues and/or organs if expression pattern of certain genes are associated with health and/or functionality of these tissues and organs. Preferably, the gene to be monitored is expressed in connective, epithelium, muscle or nerve tissue. Also preferably, the gene to be monitored is expressed in an accessory organ of the eye, annulospiral organ, auditory organ, Chievitz organ, circumventricular organ, Corti organ, critical organ, enamel organ, end organ, external female gential organ, external male genital organ, floating organ, flower-spray organ of Ruffini, genital organ, Golgi tendon organ, gustatory organ, organ of hearing, internal female genital organ, internal male genital organ, intromittent organ, Jacobson organ, neurohemal organ, neurotendinous organ, olfactory organ, otolithic organ, ptotic organ, organ of Rosenmüller, sense organ, organ of smell, spiral organ, subcommissural organ, subfornical organ, supernumerary organ, tactile organ, target organ, organ of taste, organ of touch, urinary organ, vascular organ of lamina terminalis, vestibular organ, vestibulocochlear organ, vestigial organ, organ of vision, visual organ, vomeronasal organ, wandering organ, Weber organ and organ of Zuckerkandl. More preferably, the gene to be monitored is expressed in an internal animal organ such as brain, lung, liver, spleen, bone marrow, thymus, heart, lymph, blood, bone, cartilage, pancreas, kidney, gall bladder, stomach, intestine, testis, ovary, uterus, rectum, nervous system, gland, internal blood vessels, etc.

In other embodiments, the fluorophore, e.g., GFP, BFP or RFP, can be operatively linked to the following animal transcriptional control regions that exhibit tissue specificity to monitor these tissue specific gene expressions in animals: elastase I gene control region which is active in pancreatic acinar cells (Swift et al., *Cell* 38:639–646 (1984); Ornitz et al., *Cold Spring Harbor Symp. Quant. Biol.* 50:399–409 (1986); MacDonald, *Hepatology* 7:425–515 (1987)); insulin gene control region which is active in pancreatic beta cells (Hanahan et al., *Nature* 315:115–122 (1985)), immunoglobulin gene control region which is active in lymphoid cells (Grosschedl et al., *Cell* 38:647–658 (1984); Adams et al., *Nature* 318:533–538 (1985); Alexander et al., *Mol. Cell Biol.* 7:1436–1444 (1987)), mouse mammary tumor virus control region which is active in testicular, breast, lymphoid and mast cells (Leder et al., *Cell* 45:485–495 (1986)), albumin gene control region which is active in liver (Pinckert et al., *Genes and Devel.* 1:268–276 (1987)), alpha-fetoprotein gene control region which is active in liver (Krumlauf et al., *Mol. Cell. Biol.* 5:1639–1648 (1985); Hammer et al., *Science* 235:53–58 1987)), alpha-1 antitrypsin gene control region which is active in liver (Kelsey et al., *Genes and Devel.* 1:161–171 (1987)), beta globin gene control region which is active in myeloid cells (Mogram et al., *Nature* 315:338–340 (1985); Kollias et al., *Cell* 46:89–94 (1986)), myelin basic protein gene control region which is active in oligodendrocyte cells of the brain (Readhead et al., *Cell* 48:703–712 (1987)), myosin light chain-2 gene control region which is active in skeletal muscle (Sani, *Nature* 314:283–286 (1985)), and gonadotrophic releasing hormone gene control region which is active in gonadotrophs of the hypothalamus (Mason et al., *Science* 234:1372–1378 (1986)).

5. Tumor or Cancer Associated Gene Expression

The present methods can be used in monitoring expression of genes that are specifically expressed in tumors or cancers. Preferably, the gene to be analyzed is a tumor or cancer associated gene such as an oncogene or a tumor suppressor gene. For instance, the expression of the oncogenes listed in the following Table 1 can be monitored by the present methods.

TABLE 1

Oncogenes and tumor viruses

| Acronym | Virus | Species | Tumor origin | Comments |
|---|---|---|---|---|
| abl | Abelson leukemia | Mouse | Chronic myelogenous leukemia | TyrPK(src) |
| erbA | Erythroblastosis | Chicken | | Homology to human glucocorticoid receptor |
| erbB | Erythroblastosis | Chicken | | TryPK EGF/TGFc receptor |
| ets | E26 myeloblastosis | Chicken | | Nuclear |
| fes (fps)[a] | Snyder-Thellen sarcoma Gardner-Arnstein sarcoma | Cat | | TryPK(src) |
| fgr | Gardner-Rasheed sarcoma | Cat | | TyrPK(src) |
| fms | McDonough sarcoma | Cat | | TyrPK CSF-1 receptor |
| fps (fes)[a] | Fujinami sarcoma | Chicken | | TyrPK(src) |
| fos | FBJ osteosarcoma | Mouse | | Nuclear, TR |
| hst | NVT | Human | Stomach tumor | FGF homologue |
| intl | NVT | Mouse | MMTV-induced carcinoma | Nuclear, TR |
| int2 | NVT | Mouse | MMTV-induced carcinoma | FGF homologue |
| jun | ASV17 sarcoma | Chicken | | Nuclear, TR |
| hit | Hardy-Zuckerman 4 sarcoma | Cat | | TyrPK GFR L |
| B-lym | NVT | Chicken | Bursal lymphoma | |
| mas | NVT | Human | Epidermoiod carcinoma | Potentiates response to angiotensin II |
| met | NVT | Mouse | Osteosarcoma | TyrPK GFR L |
| mil (raf)[b] | Mill Hill 2 acute leukemia | Chicken | | Ser/ThrPK |
| mos | Moloney sarcoma | Mouse | | Ser/ThrPK |
| myb | Myeloblastosis | Chicken | Leukemia | Nuclear, TR |
| myc | MC29 myelocytomatosis | Chicken | Lymphomas | Nuclear TR |
| N-myc | NVT | Human | Neuroblastomas | Nuclear |
| neu (ErbB2) | NVT | Rat | Neuroblastoma | TryPK GFR L |
| ral (mil)[b] | 3611 sarcoma | Mouse | | Ser/ThrPK |
| Ha-ras | Harvey murine sarcoma | Rat | Bladder, mammary and skin carcinomas | GTP-binding |
| Ki-ras | Kirsten murine sarcoma | Rat | Lung, colon carcinomas | GTP-binding |
| N-ras | NVT | Human | Neuroblastomas leukaemias | GTP-binding |
| rel | Reticuloendothe-liosis | Turkey | | |
| ros | UR2 | Chicken | | TyrPK GFR L |
| sis | Simian sarcoma | Monkey | | One chain of PDGF |
| src | Rous sarcoma | Chicken | | TyrPK |
| ski | SKV770 | Chicken | | Nuclear |
| trk | NVT | Human | Colon carcinoma | TyrPK GFR L |
| yes | Y73, Esh sarcoma | Chicken | | TyrPK(src) |

Similarly, the expression of the following tumor suppressor genes can be monitored by the present methods: p16, p21, p27, p53, RB, WT-1, DCC, NF-1 and APC.

Since abnormally high level of oncogene expression and abnormally low expression of tumor suppressor gene are often good indicators of oncogenesis, the present methods can be used in prognosis or diagnosis of cancer, in monitoring the development of oncogenesis and in evaluating the efficacy of the cancer therapy.

C. Methods to Evaluate a Candidate Protocol or Drug for Treating Disease or Disorder Since the method of the invention evaluates gene expression with regard to particular control sequences, the effect of various compounds, treatments (such as irradiation) or other perturbations of the genetic environment can be evaluated for their effect on expression using the methods of the invention. Thus, gene toxic agents, for example, can be identified.

In a specific embodiment, a method to evaluate a candidate protocol or drug for treating a disease or disorder is provide herein, which method comprises: a) administering said protocol or drug to a non-human mammalian subject which expresses a fluorophore under the direction of a promoter of a gene associated with a disease or disorder, and determining the expression of said promoter via observing the presence, absence or intensity of the fluorescence generated by said fluorophore at various locations in said mammalian subject by whole-body external fluorescent optical imaging; b) determining the expression of said promoter, via observing the presence, absence or intensity of the fluorescence generated by said fluorophore at various locations in said mammalian subject by whole-body external fluorescent optical imaging, in a control non-human mammalian subject which expresses said fluorophore under the direction of said promoter of said gene; and c) comparing the expression of said promoter determined in steps a) and b), wherein the expression determined in step a) is different from that in step b) identifies said protocol or drug as effective in treating the disease or disorder.

In a preferred embodiment, overexpression of the gene is associated with the disease or disorder and the expression determined in step a) is lower than that in step b) identifies said protocol or drug as effective in treating the disease or disorder.

In another preferred embodiment, underexpression of the gene is associated with the disease or disorder and the expression determined in step a) is higher than that in step b) identifies said protocol or drug as effective in treating the infection.

In still another preferred embodiment, the non-human mammalian subject which expresses a fluorophore under the direction of a promoter of a gene associated with a disease or disorder is produced by delivering a nucleic acid encoding the fluorophore operatively linked to the promoter, or a cell containing the nucleic acid, to the non-human mammalian subject (see Section B supra).

Any non-human mammalian subject can be used in the present screening methods. Preferably, the non-human mammalian subject used in the screening is a well established laboratory animal such as a mice, a rabbit or a non-human primate. Also preferably, the non-human mammalian subject used in the screening is an infectious disease animal model. Still preferably, the non-human mammalian subject used in the screen is a transgenic animal.

Any fluorophores known in the art, including the ones described in Section B, can used in the present screening methods. In a preferred embodiment, the fluorophore used in the screening is s a green fluorescent protein (GFP), a blue fluorescent protein (BFP) or a red fluorescent protein (RFP).

The present methods can be used to screen candidate protocols or drugs for treating any known diseases or disorders. In a preferred embodiment, the diseases or disorders to be screened against are cancers, immune system diseases or disorders, metabolism diseases or disorders, muscle and bone diseases or disorders, nervous system diseases or disorders, signal diseases or disorders and transporter diseases or disorders.

In yet another preferred embodiment, the non-human mammalian subject expresses a fluorophore under the direction of a promoter of an infectious organism and the expression determined in step a) is lower than that in step b) identifies said protocol or drug as effective in treating infection caused by the infectious organism.

The non-human mammalian subject used in the screening may be an infectious disease animal model.

The infectious organism screened against may be a fungus such as a yeast, a bacterium such as an eubacteria or an archaebacteria, or a virus such as a Class I virus, a Class II virus, a Class III virus, a Class IV virus, a Class V virus or a Class VI virus.

Any substances can be screened using the present screening methods for finding drug candidates for treating infection. In a preferred embodiment, a combinatorial library is used in the screening assays. Methods for synthesizing combinatorial libraries and characteristics of such combinatorial libraries are known in the art (See generally, *Combinatorial Libraries: Synthesis, Screening and Application Potential* (Cortese Ed.) Walter de Gruyter, Inc., 1995; Tietze and Lieb, *Curr. Opin. Chem. Biol.,* 2(3):363–71 (1998); Lam, *Anticancer Drug Des.,* 12(3 :145–67 (1997); Blaney and Martin, *Curr. Opin. Chem. Biol.,* 1(1):54–9 (1997); and Schultz and Schultz, *Biotechnol. Prog.,* 12(6 :729–43 (1996)).

If the infection is caused by bacteria, known antibiotics can be screened using the present screening methods for finding a suitable drug candidate. Preferably, the antibiotics to be screened are aminoglycosides (e.g., streptomycin, gentamicin, sisomicin, tobramycin, amicacin), ansamycins (e.g., rifamycin), antimycotics polyenes (e.g., nystatin, pimaricin, amphotericin B., pecilocin), benzofuran derivatives (e.g., griseofulvin), β-lactam antibiotics penicillins (e.g., penicillin G and its derivatives, oral penicillins, penicillinase-fixed penicillin broad-spectrum penicillins, penicillins active against Proteus and Pseudomonas), cephalosporins (e.g., cephalothin, cephaloridine, cephalexin, cefazolin, cefotaxime), chloramphenicol group (e.g., chloramphenicol, thiamphenicol, azidamphenicol), lmidazole fluconazole, itraconazole, linosamides (e.g., lincomycin, clindamycin), macrolides (e.g., azithromycin, erythromycin, oleandomycin, spiramycin, clarithromycin), peptides, peptolides, polypeptides (e.g., polymyxin B and E, bacitracin, tyrothricin, capreomycin, vancomycin), quinolones (e.g., nalidixic acid, ofloxacin, ciprofloxacin, norfioxin), tetracyclines (e.g., tetracycline, oxytetracycline, minocycline, doxycycline) and other antibiotics (e.g., phosphomycin, fusidic acid).

D. Methods to Screen for Gene Expression Modulators and Regulators

The above-described screening methods can also be used to identify gene expression modulators, i.e., trans-acting substances that modulate the expression of a target gene in a multi-cellular organism, or regulators, i.e., cis-acting genes of a multi-cellular organism that regulate the expression of the target gene. Besides for identifying disease or disorder treatment protocols or drugs, the screening methods described herein have wide applications in industrial, agricultural, environmental protection and many other fields. For example, transgenic animals such as transgenic cows are commercially used. It is desirable to find a suitable substance that increases the expression of the transgene and such substance can be added to the animal feed. Similarly, it is desirable to find and modify gene(s) within the transgenic cow that enhances the expression of the target transgene.

Once it is decided that alteration of the expression level of a target gene is desirable, a fluorophore can be operatively linked to the promoter, or other transcriptional control region, of the target gene and be expressed in a multi-cellular organism. Then, the multi-cellular organism expressing the fluorophore can be treated with a test substance to identify which substance modulates the fluorophore expression. Alternatively, the multi-cellular organism expressing the fluorophore itself can be mutagenized to identify genes within itself that alter the fluorophore expression. These screening principles have long been used to identify cis- or trans-acting regulators of gene expression in unicellular organisms such as bacteria or yeast. However, due to the lack of quick and simple screening methods, such screening are impractical for multi-cellular organisms such as plants and animals. The whole-body external optical imaging of gene expression disclosed herein makes such screening or mutant-haunt practical for multi-cellular organisms.

In a specific embodiment, a method to screen for a modulator of the expression of a gene in a multi-cellular organism is provided herein, which method comprises: a) administering a test substance to a non-human multi-cellular organism which expresses a fluorophore under the direction of a promoter of a gene, and determining the expression of said promoter via observing the presence, absence or intensity of the fluorescence generated by said fluorophore at various locations in said multi-cellular organism by whole-body external fluorescent optical imaging; b) determining the expression of said promoter, via observing the presence, absence or intensity of the fluorescence generated by said fluorophore at various locations by whole-body external fluorescent optical imaging, in a control multi-cellular organism which expresses said fluorophore under the direction of said promoter of said gene; and c) comparing the expression of said promoter determined in steps a) and b), wherein the expression determined in step a) is different from that in step b) identifies said test substance as a modulator of said gene expression. Preferably, the promoter is an endogenous promoter of the multi-cellular organism.

In another specific embodiment, a method to screen for a multi-cellular organism that expresses a gene at an altered level is provided herein, which method comprises: a) administering a mutation-inducing agent or treatment to a non-human multi-cellular organism which expresses a fluorophore under the direction of a promoter of a gene, and determining the expression of said promoter via observing the presence, absence or intensity of the fluorescence generated by said fluorophore at various locations in said multi-cellular organism by whole-body external fluorescent optical imaging; b) determining the expression of said promoter, via observing the presence, absence or intensity of the fluorescence generated by said fluorophore at various locations by whole-body external fluorescent optical imaging, in an untreated control multi-cellular organism which expresses said fluorophore under the direction of said promoter of said gene; and c) comparing the expression of said promoter determined in steps a) and b), wherein the expression determined in step a) is different from that in step b) identifies a multi-cellular organism that expresses said gene at said altered level. Preferably, the mutation-inducing agent or treatment causes a mutation in germ-line cells of the multi-cellular organism so that the desired mutation is stably-transferable to offspring of the multi-cellular organism.

In addition, the various protocols described in the art for "Big Blue" transgenic mice can be utilized in the system of the invention.

The following examples are included for illustrative purposes only and are not intended to limit the scope of the invention.

EXAMPLE 1

Visualization of Gene Expression in Various Tissues using Adenovirus

Four six-week-old male of female nude/nude, nude/+, or C57BL/6 mice were used. All animal studies were conducted in accordance with the principles and procedures outlined in the National Institute of Health Guide for the Care and Use of Animals under assurance number A3873-1. Mice were fed with autoclaved laboratory rodent diet (Tecklad LM-485, Western Research Products, Orange, Calif.).

The vector employed was adenorival (vAd) vector AdCMV5GFPAE1/AE3 [vAd-green fluorescent protein (GFP)] (Quantum, Montreal, Canada), which expresses enhanced GFP and the ampicillin resistance gene.

This vector was provided to various tissues to visualize expression of the CMV promoter in these tissues. Expression of reporter under control of any desired promoter can be visualized by suitable modification of this vector, as described above.

Liver: After exposure of the portal vein following an upper midline abdominal incision, total volume of 100 $\mu$l ($8\times10^{10}$ pfu/ml) vAd-GFP per mouse were injected in the portal vein using a 1 ml 39G1 latex-free syringe (Becton Dickinson, Franklin Lakes, N.J.). The puncture hole of portal vein was pressed for about 10 seconds with sterile cotton to stop any bleeding. The incision in the abdominal wall was closed with a 7-0 surgical suture in one layer. The animals were kept under Ketamine anesthesia during surgery. All procedures of the operation described above were performed with a 7× magnification microscope (Leica MZ6, Nussloch, Germany). Animals were kept in a barrier facility under HEPA filtration.

Brain: The parietal bone of the skull was exposed after an upper midline scalp incision. Twenty microliters containing $8\times10^{10}$ plaque-forming units (pfu)/ml vAd-GFP per mouse was injected in the brain by using a 1-ml 27G1/2 latex-free syringe (Becton Dickinson). The puncture hole in the skull was plugged with bone wax. The incision in the scalp was closed with a 7-0 surgical suture in one layer. The animals were kept under isofluorane anesthesia during surgery.

Pancreas: The pancreas was exposed after an upper midline abdominal incision. One-hundred microliters containing $8\times10^{10}$ pfu/ml vAd-GFP per mouse was injected in the pancreas by using a 1-ml $30G_{1/2}$ latex-free syringe (Becton Dickinson). The puncture hole was pressed for about 10 sec with sterile cotton for hemostasis. The incision was closed with a 7-0 surgical suture in one layer. The animals were kept under Kersel anesthesia during surgery. All procedures of the operation described above were performed with a ×7 magnification stereo microscope.

Prostate: The bladder and prostate were exposed after a lower midline abdominal incision. Thirty microliters containing $8\times10^{10}$ pfu/ml vAd-GFP per mouse was injected in the prostate by using a 1-ml $30G_{1/2}$ latex-free syringe (Becton Dickinson). The puncture hole in the prostate was pressed for about 10 sec with sterile cotton for hemostasis. The incision in the abdominal wall was closed with a 6-0 surgical suture in one layer. The animals were kept under isofluorane anesthesia during surgery. All procedures of the operation described above were performed with a ×7 magnification stereo miscroscope.

Bone Marrow: For bone marrow injection, animals were anesthetized by inhalation of isofluorane. The skin on the hind leg was opened with a 1-cm incision to expose the tibia. A 27-gauge needle with latex-free syringe (Becton Dickinson) then was inserted in the bone marrow cavity. A total volume of 20 $\mu$l ($8\times10^{10}$ pfu/ml) vAd-GFP per mouse was injected into the bone marrow cavity. The puncture hole in the bone was plugged with bone wax, and the incision was closed with a 6-0 surgical suture.

Visualization: For visualization at high magnification, Leica fluorescence stereo microscope, model LZ12, equipped with a 50-W mercury lamp, was used. Selective excitation of GFP was produced through a D425/60 band-pass filter and 470 DCXR dichroic mirror. Emitted fluorescence was collected through a long-pass filter GG475 (Chroma Technology, Brattleboro, Vt.) on a Hamamatsu C5810—3-chip cooled color charge-coupled device camera (Hamamatsu Photonics Systems, Bridgewater, N.J.). Images were processed for contrast and brightness and analyzed with the use of IMAGE PRO PLUS 3.1 software (Media Cybernetics, Silver Springs, Md.). Images of 1,024×724 pixels were captured directly on an IBM PC or continuously through video output on a high-resolution Sony VCR model SLV-R-1000 (Sony, Tokyo).

Imaging at lower magnification that visualized the entire animal was carried out in a light box illuminated by blue light fiber optics (Lightools Research, Encinitas, Calif.) and imaged by using the thermoelectrically cooled color charge-coupled device camera, as described above.

Figure 1B:
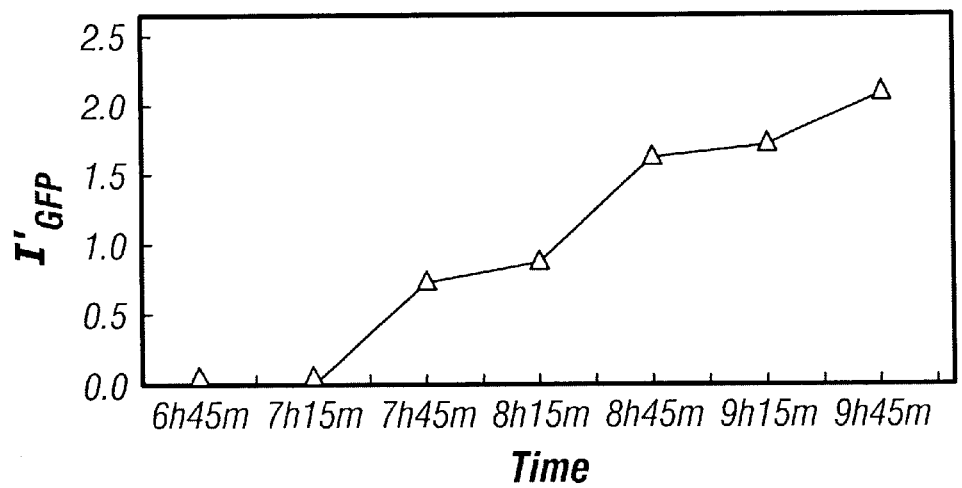

Quantitation: The intensity of GFP fluorescence is measured to account for variations in the exciting illumination with time and across the imaging area. These factors are corrected for by using the intrinsic red fluorescence of mouse skin as a base line to correct the increase over intrinsic green fluorescence caused by GFP. This can be done because there is relatively little red luminance in the GFP radiance. Consequently, the green fluorescence was calculated relative to red based on red and green channel composition in the skin image. A ratio (γ) of green to red channels was determined for each pixel in the image of skin without and with GFP. Values of γ for mouse skin throughout the image in the absence of GFP were fairly constant, varying between 0.7 and 1.0. The contribution of GFP fluorescence from within the animal increased the green component relative to red, which was reflected in higher γ values. The total amount of GFP fluorescence was approximated by multiplying the number of pixels in which value γ was higher than 1 times the γ value of each pixel. Such a product roughly corresponds to the integral GFP fluorescence [$\Gamma_{GFP}$] above the maximum value of γ for skin without GFP. The number of pixels in mouse skin images with γ value >1.0 without GFP was less than 0.02% and increased with GFP expression. The value of [$\Gamma_{GFP}$] is shown as a function of time after virus injection in FIGS. 1A and 1B for brain and liver respectively.

Images of the various organs were compared when taken at high magnification on live intact animals or similar organs viewed directly after death and dissection. The images show the distribution of gene expression in the various organs. In all cases, the images made externally are similar to those of the exposed organs.

When the live animal was viewed in a light box, it was also possible to monitor the expression of the gene, thus permitting a real time observation of the living animal and expression as it occurs in this animal. For example, a light box determination of expression of the GFP in nude mouse liver taken at 72 hours clearly shows this result. Similar results are observed in the nude mouse brain 24 hours after gene delivery. The method is quite sensitive in that the intensity of GFP fluorescence in the mouse liver at a depth of 0.8 mm under the skin was about 25% of that of the exposed organ. Gene expression is externally measurable if the average fluorescence of the GFP expressing organs is at least 20% above the average fluorescence of the surrounding skin, and at maximal level of GFP expression, the intensity in the liver exceeded more than 100 times the back dorsal and abdominal skin fluorescence.

EXAMPLE 2

Visualization of Genes Using Lentiviral Vectors

Lentiviral vectors have been shown to transduce a broad spectrum of non-dividing cells in vitro, such as neurons, retina, liver, muscle and hematopoietic stem cells (see, for example, Naldini, L. et al., *Science* (1996) 272:263–267; Kafri T. et al.; *Nat. Genet* (1997) 17:314–317; Takahashi, M. et al., *J. Virol* (1999) 73:7812–7816; Miyoshi, H. et al. *Science* (1999) 283:682–686). Although it has been reported that hepatocytes are refractory to lentiviral transductioni unless they progress into the cell cycle (Park, F. et al. *Nat. Genet* (2000) 24:49–52), it is shown below that lentiviral gene delivery to the liver for expression visualization is practical.

Figure 2A:
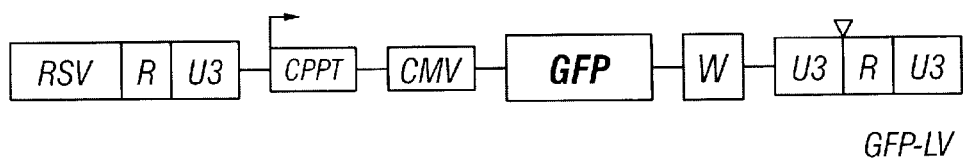
FIGS. 2A and 2B art pertinent to administration of lentiviral vectors.

A lentiviral vector based on HIV1 designated GFP-LV was used. This vector contains a self-inactivating mutation in the U-3 region, a post-transcriptional element, and an internal CMV promoter. It also contains cppt, the central polypurine tract derived from HIV-pol and a woodchuck hepatitis virus post-transcriptional element (WPRE). A diagram of this vector is shown in FIG. 2A.

Figure 2B:
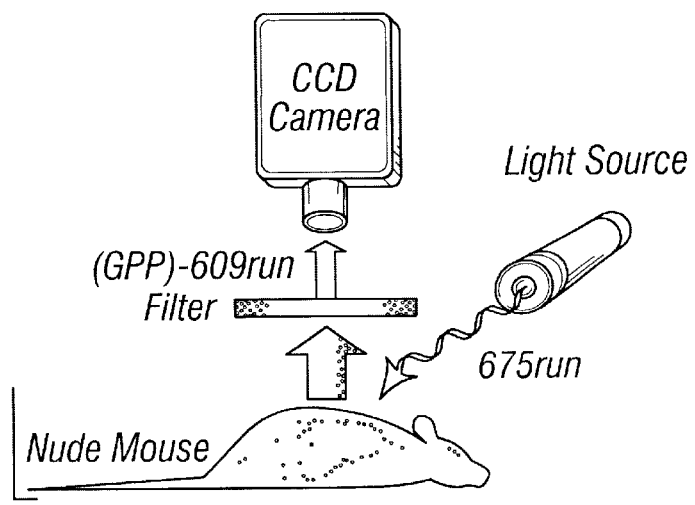

The vector GHP-LV at $1 \times 10^9$ IU was injected into the portal vein of nude mice; (Hsd:asymic nude-nu). Six (6) days after injection green fluorescence was testable in the liver using in-vivo fluorescence optical imaging, as shown in FIG. 2B. At day 21, all lobes of the liver of the mice injected with this vector exhibited a homogeneous green fluorescence.

GHP-LV at $1 \times 10^9$ IU was also injected intraperitoneally and this method also resulted in a high level of transduction of liver and spleen.

Western Blot demonstrated dose dependence of GFP expression in the range of $0.5–2.5 \times 10^9$ IU. Vector integration in the liver 3 weeks after injection was demonstrated by PCR.

Confirmation that the transduced cells were not rapidly dividing was achieved by administering 5' bromo-2' deoxyuridine (BrdU) 15 mgs/kg by daily IP injections in order to label dividing cells. While the cells in the duodenum showed high labelling, only about 3% of liver cells were BrdU positive in either control or lentiviral-treated livers.

EXAMPLE 3

Additional Applications

In addition to the procedures exemplified in Examples 1 and 2, the methods of the invention may be used to monitor expression of control sequences that are regulated by the unfolded protein response (UPR) as described, for example, by Niwa, M., et al., *Cell* (1999) 99:691–702, the contents of which are incorporated herein by reference. Another suitable target for study is the circadian rhythm controlling genes which were studied using less convenient techniques by Yamaguchi, S., et al, *Nature* (2001) 409:684, incorporated herein by reference.

Since modifications will be apparent to those of skill in this art, it is intended that this invention be limited only by the scope of the appended claims.

What is claimed is:

1. A method to monitor the ability of a promoter to promote expression in an animal of an endogenous gene that is controlled by said promoter, which method comprises:

a) delivering, to an animal, cells containing a nucleic acid encoding a fluorophore operatively linked to the promoter of said endogenous gene whose ability to promote expression is to be analyzed; and b) observing the presence, absence or intensity of the fluorescence generated by said fluorophore at various locations in said animal by whole-body external fluorescent optical imaging, whereby the ability of said promoter to promote expression is monitored, and wherein said fluorophore is a protein that is autofluorescent such that no substrates or cofactors are needed for it to fluoresce.

2. The method of claim 1, wherein the cells are delivered to the animal via a surgical procedure.

3. The method of claim 2, wherein the cells are delivered to the animal via direct implantation by surgical orthotopic implantation (SOI) at a desired site.

4. The method of claim 1, wherein the animal is a human and the fluorophore is a humanized fluorophore.

5. The method of claim 1, wherein the fluorophore is selected from the group consisting of a green fluorescent protein (GFP), a blue fluorescent protein (BFP) and a red fluorescent protein (RFP).

6. The method of claim 5, wherein the animal is a human and the GFP is the humanized hGFP-S65T.

7. The method of claim 1, wherein the animal is a mammal.

8. The method of claim 7, wherein the mammal is selected from the group consisting of a mouse, a rat, a rabbit, a cat, a dog, a pig, a cow, an ox, a sheep, a goat, a horse, a monkey and a non-human primate.

9. The method of claim 1, wherein the endogenous gene is normally expressed in a tissue or organ specific manner.

10. The method of claim 9, wherein the tissue is selected from the group consisting of connective, epithelium, muscle and nerve tissues.

11. The method of claim 9, wherein the organ is selected from the group consisting of brain, lung, liver, spleen, bone marrow, thymus, heart, lymph, blood, bone, cartilage, pancreas, kidney, gall bladder, stomach, intestine, testis, ovary, uterus, rectum, nervous system, gland, and internal blood vessels.

12. The method of claim 1, wherein the endogenous gene is an endogenous tumor or cancer associated gene.

13. The method of claim 12, wherein the tumor or cancer associated gene is an oncogene or a tumor suppressor gene.

* * * * *